United States Patent [19]
Richardson

[11] 3,962,322
[45] June 8, 1976

[54] PROCESS FOR UNSATURATED ALDEHYDE OXIDATION USING A SUPPORTED CATALYST

[75] Inventor: Peter C. Richardson, Morristown, N.J.

[73] Assignee: Celanese Corporation, New York, N.Y.

[22] Filed: Sept. 25, 1974

[21] Appl. No.: 508,929

[52] U.S. Cl. .......................... 260/530 N; 252/456; 260/413; 260/533 N
[51] Int. Cl.² ........................................ C07C 51/32
[58] Field of Search .................... 260/530 N, 413

[56] References Cited
UNITED STATES PATENTS

| | | | |
|---|---|---|---|
| 3,383,330 | 5/1968 | Kang | 260/533 N |
| 3,644,509 | 2/1972 | Allen | 260/530 N |
| 3,691,096 | 9/1972 | Sennewald et al. | 260/533 N |
| 3,773,828 | 11/1973 | Kadowaki et al. | 260/530 N |

*Primary Examiner*—Vivian Garner

[57] ABSTRACT

An improved process for the conversion of an unsaturated aldehyde (such as acrolein) to the corresponding unsaturated carboxylic acid (such as acrylic acid) is disclosed. The improved process comprises reacting in the gas phase at a temperature sufficient to accomplish the desired reaction of the aldehyde with oxygen in the presence of unagglomerated particles of a supported catalyst having the empirical formula $Mo_aV_bW_cMn_dO_e$, the atomic ratio of Mo:V:W:Mn:O being such that when $a$ is 12, $b$ is 0.5 to 12, $c$ is 0.1 to 6, $d$ is 0.5 to 20 and $e$ is 37 to 94, the catalytic metals being supported on porous silica particles having a surface area of from about 25 to about 350 m²/gm and a porosity of from about 0.2 to about 1.0 cc/gm whereby essentially all of the catalytic metals are contained on the surfaces of the particles.

10 Claims, No Drawings

PROCESS FOR UNSATURATED ALDEHYDE OXIDATION USING A SUPPORTED CATALYST

BACKGROUND OF THE INVENTION

Numerous processes and catalysts are known in the prior art for the production of unsaturated, carboxylic acids by the oxidation of unsaturated aldehydes, e.g., the production of acrylic acid from acrolein. A very efficacious process of this type is shown in U.S. Pat. No. 3,644,509 which discloses producing an unsaturated carboxylic acid, such as acrylic acid, by reacting the corresponding unsaturated aldehyde, such as acrolein, with oxygen in the presence of a catalyst having the empirical formula $Mo_aV_bW_cMn_dO_e$, the atomic ratio of MO:V:W:Mn:O being such that when $a$ is 12, $b$ is 0.5 to 12, $c$ is 0.1 to 6, $d$ is 0.5 to 20 and $e$ is 37 to 94.

The search has continued for improved catalysts and processes to produce unsaturated carboxylic acids by the oxidation of unsaturated aldehydes.

Metal oxide catalysts are often used "neat" (i.e., unsupported) in processes of this type and often as particulates in a bed or zone within a reaction vessel. Generally, the reactants are introduced, either separately or concurrently, at one end of the zone and flow co-currently through the reaction zone in contact with the particular catalytic material therein with the reaction product stream (including the desired product) exiting from the zone at the end opposite introduction.

A number of difficulties have been found to arise in the operation of such neat metal oxide-catalyzed processes. It has been found, for example, that substantially (i.e, more than 75 percent) of the total conversion occurs in the first portion of the catalyst zone or bed (i.e., the first 25 percent of the total catalyst zone or bed) which is in contact with the reactants. The concentration of conversion in the first portion of the zone in an exothermic reaction raises the exotherm temperature at that point substantially in excess of that at later points in the catalyst zone. These high exotherm temperatures make control of the reaction more difficult, dictate more expensive heat-resistant materials, often decrease the yield of desired product and/or increase the yield of undesired by-products and are otherwise disadvantageous.

Generally, attempts to solve the problems associated with such a concentration of conversion in the initial portion of a neat catalyst zone have focused on diluting the catalyst in such a manner so as to essentially homogenize the exotherm temperature throughout the length of the catalyst zone. Dilution has been attempted both by adding separate discrete particles of a non-catalytic material uniformly dispersed with the catalyst particles and by mixing the catalyst material with the non-catalytic material (in solution, slurry or the like) and forming the resulting mixture into relatively homogeneous particles of an admixture of catalytic and noncatalytic material for use in the catalytic reaction zone.

These types of dilution of catalytic material in a reaction zone have been found, however, to manifest other problems. That is, it is frequently considerably more expensive to prepare the diluted catalyst zones or beds. In addition, product yields from such diluted catalyst zones often are lower both in total product yield and product selectivity than with the corresponding neat catalyst zones.

OBJECTS AND SUMMARY OF THE INVENTION

It is an object of this invention to provide a process for the conversion of an unsaturated aldehyde to the corresponding unsaturated carboxylic acid which reduces or alleviates the problems of the prior art.

It is a specific object of the present invention to provide a process for the conversion of an unsaturated aldehyde to the corresponding unsaturated carboxylic acid which maintains a relatively even exotherm temperature throughout the reaction zone, the maximum exotherm temperature being 30°C.

It is also an object of this invention to provide a process for the conversion of an unsaturated aldehyde to the corresponding unsaturated carboxylic acid which provides a high yield of and selectivity for the desired product.

It is further an object of this invention to provide a process for the conversion of an unsaturated aldehyde to the corresponding unsaturated carboxylic acid which conversion is relatively inexpensive to perform.

It is further an object of this invention to provide a process for the conversion of an unsaturated aldehyde to the corresponding unsaturated carboxylic acid utilizing a single form of catalytic component throughout substantially all of the catalytic reaction zone.

The present invention provides an improved process for the conversion of an unsaturated aldehyde to the corresponding unsaturated carboxylic acid which comprises reacting in the gas phase at a temperature sufficient to accomplish the desired reaction of an aldehyde of the following formula:

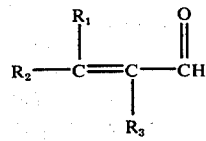

wherein $R_1$ is hydrogen or an alkyl radical of from 1 to 6 carbon atoms and $R_2$ and $R_3$ are hydrogen or methyl radicals; with oxygen in the presence of a supported catalyst having the empirical formula $Mo_aV_bW_cMn_dO_e$, the atomic ratio of Mo:V:W:Mn:O being such that when $a$ is 12, $b$ is 0.5 to 12, $c$ is 0.1 to 6, $d$ is 0.5 to 20 and $e$ is 37 to 94, the improvement which comprises using as the catalyst unagglomerated particles of the above empirical formula supported on porous silica particles having a surface area of from about 25 to about 350 m²/gm and a porosity of from about 0.2 to about 1.0 cc/gm, the catalytic metals being contained essentially on the surfaces of the particles.

The essence of the present invention is the discovery that a particular type and composition of support material for this particular catalyst material used in this particular reaction offers a surprising balance of high yield and high selectivity of desired product while maintaining a reasonably even exotherm temperature along the reaction zone. In addition, it has been found that the improved process of the present invention can be performed with lower amounts of catalyst per mole of reactants than the corresponding neat catalyst process without decreasing product yield or selectivity.

DESCRIPTION OF PREFERRED EMBODIMENTS

The catalyst as described above and as used in the present invention may be regarded as a mixture of oxides of the various metals and/or mixtures of heteropoly acid salts of the various metals (both of which mixtures are hereinafter called "catalytic metals") supported on the external surfaces of an unagglomerated porous silica support material.

That is, once the various catalytic metals (in the form of oxides or salts) are applied onto the porous silica support particles (in a manner as described hereinbelow), the particles are not agglomerated, compacted or otherwise physically combined into larger-sized particles. In this manner, essentially all of the catalytic metals remain disposed on the external surfaces of the porous silica support material. Such external surfaces include the outer (e.g., peripheral) surfaces and also some or all of the surfaces of the pores in the particles. In the particles used in the process of the present invention, however, essentially all of the catalytic metals are exposed to the vapor phase reactants and essentially none of the catalytic metals are disposed within the non-porous interior of a particle (as occurs when catalyst-containing particles are thereafter agglomerated into larger particles).

Since the catalyst particles as used in the process of the present invention are not agglomerated or otherwise further combined into largersized particles, the size and shape of the silica support particles on which the catalytic metals are deposited is essentially determined by the size and shape of the ultimate catalyst particles desired. The particle shape and size of the porous silica particles will vary somewhat depending upon the particular reaction, reaction vessel and the like, and it will be understood that the porous silica particles (and the resulting catalyst particles) may be of any size and shape effective to catalyze a particular reaction. Particle size can be, for example, from about 0.01 to about 1 inch. Generally, for commerical reactors the porous silica particles (and the resulting catalyst-containing particles) will be spherical, cylindrical, or elliptical in shape. Spherical particles of this type generally will have a diameter in the range of from about ⅛ to about ½, preferably from about ¼ to about ⅜ inch. Cylindrical- (or elliptical-) shaped particles of this type will generally have their diameter (or both diameters for elliptical-shaped particles) in the range of from about ⅛ to about ½, preferably from about ¼ to about ⅜, inch and a length of from about ⅛ to about ½, preferably from about ¼ to about ⅜, inch.

The porous silica particles useful as the catalyst support have a surface area of from about 25 to about 350, preferably from about 100 to about 200, m²/gm and a porosity of from about 0.2 to about 100, preferably from about 0.3 to about 0.8, cc/gm. Porosity is measured in accordance with conventional techniques known in the art such as mercury porosimetry.

The catalyst may be prepared by any suitable technique for depositing the catalytic material onto the surfaces of the support but is preferably prepared by depositing the metal oxide compounds or their precursors on and in the porous silica particles and calcining the particles at a temperature of about 200° to 600°C. or more in the presence of oxygen. For example, aqueous solutions of water-soluble compounds of the metals may be mixed, the porous silica particles added thereto and the water removed by evaporation or the like to leave dry particles suitable for calcining. Suitable water-soluble compounds useful in the preparation of a catalyst in accordance with the foregoing method include ammonium paramolybdate, ammonium metavanadate, ammonium paratungstate, manganous acetate, ammonium metatungstate, orthotungstic acid, metataungstic acid, molybdic acid, molybdenum pentoxide, molybdenum trioxide, manganous benzoate, and manganese nitrate.

The catalyst particles are preferably formed by first forming an aqueous solution of water-soluble salts of molybdenum, vanadium and tungsten, adding the porous silica particles thereto to absorb the solution, adding a solution of a manganese salt which causes precipitation of the metal compounds, drying and calcining the particles. Suitable water-soluble manganese compounds useful in the preparation of a catalyst in this manner include the water-soluble manganese salts of an inorganic or organic acid. Preferably the manganese salts of $C_1$ to $C_8$ carboxylic acids or nitric acid are utilized. The water-soluble compounds of molybdenum, vanadium and tungsten useful in this method of preparation of the catalyst particles again include ammonium paramolybdate, ammonium metavanadate, ammonium paratungstate, manganous acetate, ammonium metatungstate, orthotungstic acid, metatungstic acid, molybdic acid, molybdenum pentoxide and molybdenum trioxide. The ammonium salts of these metals are preferred for use in this method of catalyst preparation.

As noted above, the supported catalyst has the empirical formula $Mo_aV_bW_cMn_dO_e$, the atomic ratio of Mo:V:W:Mn:O being such that when $a$ is 12, $b$ is 0.5 to 12, $c$ is 0.1 to 6, $d$ is 0.5 to 20 and $e$ is 37 to 94. In a particularly preferred catalyst, the atomic ratio of Mo:V:W:Mn:O is such that when $a$ is 12, $b$ is 1 to 6, $c$ is 0.3 to 3.0, $d$ is 1 to 12 and $e$ is 40 to 84. Generally, the catalyst particles contain from about 5 to about 75, preferably from about 25 to about 60, most preferably from about 35 to about 50, weight percent of the catalyst materials and concommitantly from about 95 to about 25, preferably from about 75 to about 40, most preferably from about 65 to about 50, weight percent of the porous silica support material.

The present process may be carried out continuously or non-continuously and the catalyst may be present in various forms such as in one or more fixed beds or as a fluidized system.

Portions of the reactants which do not undergo reaction may be recycled if desired. The temperatures employed are preferably between 250° and 325°C. although higher or lower temperatures generally between 200° and 350°C. may be employed.

The pressure utilized in the present process may be subatmospheric, atmospheric or superatmospheric. Usually pressures ranging from 0.5 to 3.0 atmospheres will be utilized although pressure up to 10 atmospheres and higher may be suitably employed. The contact time of the reactants with the catalyst at the reaction conditions is generallly between 0.3 and 15 seconds but is preferably a relatively short time of from 0.5 to 10 seconds. By contact time as used herein is meant the contact time adjusted to 25°C. and atmospheric pressure (conditions denoted by NTP). Thus, the contact time is calculated by dividing the volume of the catalyst bed (including voids) by the volume per unit time flow rate of the reactants at NTP.

The oxygen necessary as a reactant in the present process may be from practically any molecular oxygen-containing gas such as concentrated molecular oxygen or air. Also, the molecular oxygen-containing gas may be one wherein molecular oxygen is mixed in varying amounts with an inert diluent gas such as nitrogen, argon, or a carbon oxide. The unsaturated aldehyde reactant may be premixed with the oxygen-containing gas before introduction into the reaction zone or the reactants may be introduced separately into the reaction zone. Also, the unsaturated aldehyde and/or molecular oxygen may be introduced into the reaction zone at one or a plurality of points along the length of the reaction zone. The reactants may be pretreated before entering the reaction zone such as for the removal of undesirable components therefrom.

Although other unsaturated acyclic aldehydes may be oxidized to the corresponding carboxylic acids by the present process, the aldehydes preferably have $\alpha,\beta$-unsaturation with the most suitable aldehydes being in of the formula:

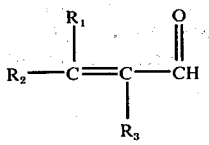

wherein $R_1$ is hydrogen or an alkyl radical of 1 to 6 carbon atoms and wherein $R_2$ and $R_3$ are hydrogen or methyl radicals. Preferably the present process is utilized for the production of acrylic acid from acrolein. Other conversions that may be accomplished include methacrolein to methacrylic acid, and crotonaldehyde to crotonic acid.

In conducting the oxidation reaction, the gaseous feed mixture should generally contain from 0.5 to 6 moles of oxygen per mole of the unsaturated aldehyde although the preferable range is from 1.0 to 4.0 moles per mole. Water is also desirably present in the gaseous feed in amounts of from 1 to 25, preferably 2 to 20, moles per mole of unsaturated aldehyde. In addition to water, diluents which are gaseous under the reaction conditions and are relatively inert may be introduced into the system. Suitable diluents include nitrogen, flue gas, $CO_2$ and paraffinic hydrocarbons.

While unsaturated aldehydes as described above are commerically available, it is advantageous to utilize as the starting material herein, the reaction product stream from a reaction zone in which an alkene of the following formula:

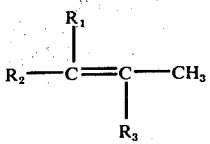

wherein $R_1$ is hydrogen or an alkyl radical of from 1 to 6 carbon atoms; and $R_2$ and $R_3$ are hydrogen or methyl radicals; is catalytically oxidized to the corresponding unsaturated aldehyde. Such an alkene oxidation process may be conducted in any suitable manner as known in the art.

When the alkene oxidation product stream is utilized as the starting material in the present invention it is preferred that the alkene oxidation to unsaturated aldehyde reaction zone and unsaturated aldehyde oxidation to unsaturated carboxylic acid reaction zone be maintained serially such that the reaction product stream from the alkene oxidation zone may be utilized directly (i.e., without intermediate separation and/or product recovery) as the starting unsaturated aldehyde feed material in the unsaturated aldehyde oxidation zone.

The unsaturated carboxylic acid product resulting from the aldehyde oxidation process of the present invention is useful in a number of industrial uses and particularly as a starting material for the ultimate production of plastic resin materials such as acrylic resins, methacrylate resins, methyl methacrylate resins and the like.

The invention is additionally illustrated in connection with the following Examples which are to be considered as illustrative of the present invention. It should be understood, however, that the invention is not limited to the specific details of the Examples.

EXAMPLE 1

Solutions of 15.79 grams of ammonium molybdate in 56 cc water, 2.65 grams of ammonium metavanadate in 56 cc water and 2.23 grams of ammonium paratungstate in 56 cc water are mixed together at 70°C. 32.5 grams of silica particles are added while stirring the solution. The silica has a surface area of 150 m²/gm, a particle size of −20+30 mesh (about 0.03 to 0.02 inch) and a porosity of 0.51 cc/gm measured by mercury porosimetry. A solution of 5.50 grams of manganese acetate is added to the mixture and the resulting slurry is evaporated to dryness in a stream of dry air. The solid material thus obtained is calcined in air at 400°C. for 5 hours. The composition of the resulting catalyst is represented by the formula $Mo_{12}V_3W_{1.2}Mn_3O_{53}/SiO_2$. The catalyst contains 65 percent by weight silica and 35 percent by weight of catalytic material.

A 5 cc sample of the above-produced −20+30 mesh particle size catalyst is tested for the oxidation of acrolein to acrylic acid in a laboratory reactor which consists of a stainless steel U-tube of 0.364 inch internal diameter heated in a fluidized sand bath. A gaseous mixture of 2.6 mole percent acrolein, 45.2 mole percent steam and 52.2 mole percent air is passed over the catalyst with an NTP contact time of 0.87 seconds. The liquid product collected and the vent gases are each analyzed by gas chromatography. The results obtained are given below, where:

Conversion = 100 × (Total moles of carbon recovered —moles of carbon recovered as acrolein)/(Total moles of carbon recovered)

Selectivity = 100 × (Moles of carbon in product as acrylic acid/(Total moles of carbon recovered — Moles of carbon recovered as acrolein)

Yield = 100 × (Moles of carbon in product as acrylic acid/Total moles of carbon recovered)

| Run No. | Reaction Temperature, °C. | Conversion % | Selectivity % | Yield % |
| --- | --- | --- | --- | --- |
| 1 | 285 | 99 | 95 | 95 |
| 2 | 285 | 98 | 96 | 94 |
| 3 | 290 | 100 | 95 | 95 |
| 4 | 290 | 100 | 96 | 96 |

EXAMPLE 2

A catalyst of the same chemical composition as Example 1 is prepared by the procedure described in Example 1 except that the silica has a particle size of −20 to +30 mesh, a surface area of 60 m²/gm and a porosity of 0.69 cc/gm. The catalyst is tested for acrolein oxidation under the conditions described in Example 1, with the following results:

| Run No. | Reaction Temperature, °C. | Conversion % | Selectivity % | Yield % |
| --- | --- | --- | --- | --- |
| 5 | 314 | 100 | 91 | 91 |
| 6 | 315 | 100 | 92 | 92 |
| 7 | 315 | 99 | 92 | 92 |
| 8 | 314 | 100 | 92 | 92 |

This Example serves to illustrate the importance of the surface area and pore volume of the support on the activity and selectively of the catalyst. The catalyst of Example 1 employs a relatively high surface area silica, and shows higher activity (as evidenced by the temperature necessary to operate at 100 percent acrolein conversion since the lower the operating temperature the more active the catalyst), selectivity and yield than the catalyst of Example 2 which employs a silica of lower surface area.

COMPARATIVE EXAMPLE A

A catalyst of the same chemical composition as that in Example 1 is prepared using the metal salts described therein. The silica is added in the form of 108.3 grams of a 30 weight percent aqueous colloidal suspension of silica. After evaporating to dryness and calcining in the manner described in Example 1, the fine particles are agglomerated to spherical particles of −20+30 mesh size. The agglomerated catalyst particles prepared in this manner each appear (upon visual and microscopic examination) to be a uniform dispersion of catalytic and non-catalytic (i.e., silica) material. A substantial portion of the catalytic metals appear to be disposed within the solid portion of the body of the particles so as not to be exposed to vapor phase reactants.

The resulting catalyst particles have a particle size of about −20 to +30 mesh, a surface area of 93m²/gm and a porosity of 0.34 cc/gm. The catalyst is tested for acrolein oxidation under the conditions described in Example 1 with the following results:

| Run No. | Reaction Temperature, °C. | Conversion % | Selectivity % | Yield % |
| --- | --- | --- | --- | --- |
| 9 | 299 | 84 | 95 | 80 |
| 10 | 315 | 96 | 93 | 90 |
| 11 | 315 | 96 | 94 | 90 |
| 12 | 322 | 98 | 94 | 91 |
| 13 | 322 | 98 | 93 | 91 |
| 14 | 330 | 98 | 92 | 90 |

This Example serves to illustrate the importance of the use of a catalyst particle containing the catalytic metals on the external surfaces of the finished catalyst. The catalyst of this Example which, because of the colloidal size of the silica and the subsequent agglomeration after deposition of the catalytic metals, contains catalytic metals in its interior portions not exposed to the reactants, shows lower activity, as evidenced by the higher operating temperature required for complete acrolein conversion, also lower selectivity and yield than the catalyst of Example 1 employing the preferred method of preparation.

COMPARATIVE EXAMPLE B

Comparative Example A is repeated except that the silica is added in the form of fine particles all smaller than 30 mesh having a distribution generally of from about −30+250 mesh (with about 15 weight percent of the particles going through the 250 mesh screen) and with an average particle size of about 100 microns, a surface area of 70 m²/gm and a porosity of 0.69 cc/gm. The silica used is the silica of Example 2 ground to the finer size. After evaporating to dryness and calcining in the manner described in Example 1, the particles are consolidated into particles of −20+30 mesh size. The catalyst is tested for acrolein oxidation under the conditions described in Example 1, with the following results:

| Run No. | Reaction Temperature, °C. | Conversion % | Selectivity % | Yield % |
| --- | --- | --- | --- | --- |
| 15 | 315 | 94 | 93 | 88 |
| 16 | 315 | 93 | 93 | 87 |
| 17 | 325 | 98 | 91 | 89 |
| 18 | 325 | 91 | 92 | 83 |

-continued

| Run No. | Reaction Temperature, °C. | Conversion % | Selectivity % | Yield % |
|---|---|---|---|---|
| 19 | 325 | 96 | 92 | 88 |
| 20 | 335 | 100 | 88 | 88 |
| 21 | 335 | 100 | 91 | 91 |

This Example serves to illustrate again the importance of utilizing unagglomerated catalyst particles containing the catalytic metals on the surfaces of the particular silica support particles. The acrolein conversion process using the catalyst prepared by the method of Example 1 shows higher activity, selectivity and yield than the process using the catalyst of this Example prepared as described in this other manner.

COMPARATIVE EXAMPLE C

A catalyst is prepared by the method of Example 1 except that the silica support is not included. The chemical composition of the Mo-V-W-Mn oxides in the unsupported catalyst of this Example and the supported catalyst of Example 1 are identical.

Acrolein oxidation is performed in accordance with the procedure of Example 1 utilizing the above-prepared unsupported catalyst as well as the catalyst of Example 1 and Comparative Example A. The temperature profile through the catalyst bed in each run is measured using a 5 junction thermocouple arranged along the vertical axis of the catalyst bed both in the center of the bed and along the exterior wall of the reaction zone. The difference between the bed temperature and wall temperature at a given point is the exotherm temperature. The maximum exotherm temperature for each run and other result are given below:

| Catalyst | Temperature, °C. | Conversion % | Selectivity % | Yield % | Maximum Exotherm Temperature °C. |
|---|---|---|---|---|---|
| Comparative Example C | 247 | 100 | 93 | 93 | 41 |
| Example 1 | 285 | 100 | 97 | 97 | 15 |
| Comparative Example A | 335 | 100 | 92 | 92 | 31 |

This Example illustrates that the acrolein oxidation process of the present invention utilizing the particular unagglomerated silica supported catalysts give the highest selectivity and yield to acrylic acid and significantly moderate the temperature in the catalyst bed. They are superior in these respects to unsupported catalysts (Comparative Example C) and an agglomerated, supported catalyst (Comparative Example A). The decrease in the exotherm generated in the catalyst bed is very significant in operation of a catalyst, as undesirable temperature changes may result in catalyst deactivation or physical deterioration and loss in efficiency to desired products. In addition, analysis of the product streams in each run shows that the acrolein oxidation process of the present invention produces substantially less propionic acid as an impurity than the run utilizing the catalyst of Comparative Example C. As known in the art, propionic acid is a detrimental impurity in acrylic acid particularly when the acrylic acid is further utilized to form plastic resin materials. For such use, the acrylic acid should contain as small an amount of propionic acid as possible.

EXAMPLE 3

A solution containing 136.1 grams ammonium molybdate, 22.85 grams ammonium metavanadate and 19.23 grams ammonium paratungstate in 1450 cc water is concentrated by evaporating off excess water until its volume is 200 cc. 280 grams of silica in the form of 5 mm spheres are added to this solution, which is totally absorbed by the silica pellets. The silica has a surface area of 150 m²/gm. and a porosity of 0.51 cc/gm. 47.45 grams of manganese acetate dissolved in a minimum amount of water is then added. The catalyst is dried at 120°C. and calcined in air at 400°C. for 5 hours. The catalyst contains 33 weight percent catalyst material and 67 weight percent silica support.

A liter of catalyst is placed in a 1 inch O.D. steel reactor tube heated at 286°C. A gaseous feed mixture containing 4.1 mole percent acrolein, 48.0 mole percent nitrogen, 6.6 mole percent oxygen and 41.3 mole percent water is passed over the catalyst with a contact time of 2.48 seconds. 86 percent of acrolein fed is converted with 86 percent efficiency to acrylic acid.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a process for the conversion of an unsaturated aldehyde to the corresponding unsaturated carboxylic acid which comprises reacting in the gas phase at a temperature sufficient to accomplish the desired reaction an aldehyde of the following formula:

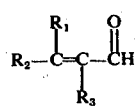

wherein $R_1$ is hydrogen or an alkyl radical of from 1 to 6 carbon atoms and $R_2$ and $R_3$ are hydrogen or methyl radicals; with oxygen in the presence of a supported catalyst having the empirical formula $Mo_aV_bW_cMn_dO_e$, the atomic ratio of Mo:V:W:Mn:O being such that when $a$ is 12, $b$ is 0.5 to 12, $c$ is 0.1 to 6, $d$ is 0.5 to 20 and $e$ is 37 to 94, the improvement which comprises using as the catalyst unagglomerated particles of the above empirical formula supported on porous silica particles having a surface area of from about 25 to about 350 m²/gm and a porosity of from about 0.2 to about 1.0 cc/gm, the catalytic metals being contained essentially only on the surfaces of the particles, and wherein said process is performed in a reaction vessel and the maximum exotherm temperature is 30°C.

2. The improved process according to claim 1 wherein said temperature is within the range of from 200° to 350°C.

3. The improved process according to claim 1 wherein water is present in an amount of from 1 to 25 moles per mole of unsaturated aldehyde.

4. The improved process of claim 1 wherein said aldehyde is acrolein or methacrolein, wherein the temperature is within the range of about 200° to 350°C., the pressure is within the range of about 0.5 to 10 atmospheres, wherein water is present in amounts of from about 1 to 25 moles per mole of said aldehyde and wherein oxygen is present in amounts of from about 0.5 to 6.0 moles per mole of said aldehyde.

5. The improved process of claim 1 wherein said silica particles have a surface area of from about 100 to about 200 m²/gm and a porosity of from about 0.3 to about 0.8 cc/gm.

6. The improved process of claim 1 wherein when $a$ is 12, $b$ is 1 to 6, $c$ is 0.3 to 3.0, $d$ is 1 to 12 and $e$ is 40 to 84.

7. The process of claim 6 wherein said silica particles have a surface area of from about 100 to about 200 m²/gm and a porosity of from about 0.3 to about 0.8 cc/gm.

8. The improved process of claim 1 wherein said aldehyde is formed in a first reaction zone by the catalytic oxidation of an alkene of the following formula:

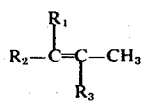

wherein $R_1$, $R_2$ and $R_3$ are defined as above.

9. A process for the conversion of acrolein to acrylic acid comprising reacting in the gas phase acrolein with oxygen in the presence of a metal oxide catalyst of the empirical formula

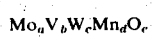

the atomic ratio of Mo:V:W:Mn:O in said catalyst being such that when $a$ is 12, $b$ is from 1 to 6, $c$ is from 0.3 to 3.0, $d$ is from 1 to 12 and $e$ is from 40 to 84, said metal oxide catalyst being contained and supported essentially only on the surfaces of porous silica particles of up to about 1 inch in maximum dimension, said porous silica particles having a surface area of from about 100 to about 200 m²/gm and a porosity of from about 0.3 to about 0.8 cc/gm, said process being conducted at temperatures from about 250°C to 325°C, pressures from 0.5 to 3.0 atmospheres, water being present in amounts of from 1 to 25 moles per mole of acrolein, and wherein said process is performed in a reaction vessel and the maximum exotherm temperature is 30°C.

10. A process according to claim 9 wherein water is present in an amount of from 2 to 20 moles per mole of acrolein.

* * * * *